United States Patent
Schultz

(10) Patent No.: US 11,618,910 B2
(45) Date of Patent: Apr. 4, 2023

(54) METHODS AND SYSTEMS FOR THE PRODUCTION OF ALCOHOLS AND/OR ACIDS

(71) Applicant: LanzaTech NZ, Inc., Skokie, IL (US)

(72) Inventor: Michael Anthony Schultz, Indianapolis, IN (US)

(73) Assignee: LanzaTech NZ, Inc., Skokie, IL (US)

( * ) Notice: Subject to any disclaimer, the term of this patent is extended or adjusted under 35 U.S.C. 154(b) by 943 days.

(21) Appl. No.: 16/353,263

(22) Filed: Mar. 14, 2019

(65) Prior Publication Data
US 2019/0203235 A1 Jul. 4, 2019

Related U.S. Application Data

(63) Continuation of application No. 13/882,688, filed as application No. PCT/US2011/057220 on Oct. 21, 2011, now abandoned.

(60) Provisional application No. 61/405,904, filed on Oct. 22, 2010.

(30) Foreign Application Priority Data

Nov. 4, 2010 (NZ) .......................... 589003

(51) Int. Cl.
| | | |
|---|---|---|
| *C12P 7/54* | (2006.01) | |
| *C07C 29/151* | (2006.01) | |
| *C12M 1/107* | (2006.01) | |
| *C12P 7/18* | (2006.01) | |
| *C12P 7/06* | (2006.01) | |
| *B65D 81/32* | (2006.01) | |
| *C12M 1/00* | (2006.01) | |
| *C12P 7/08* | (2006.01) | |
| *C07C 51/12* | (2006.01) | |

(52) U.S. Cl.
CPC ................ *C12P 7/54* (2013.01); *B65D 81/32* (2013.01); *C07C 29/1518* (2013.01); *C07C 51/12* (2013.01); *C12M 21/04* (2013.01); *C12M 21/12* (2013.01); *C12M 43/00* (2013.01); *C12P 7/065* (2013.01); *C12P 7/08* (2013.01); *C12P 7/18* (2013.01); *Y02E 50/10* (2013.01); *Y02E 50/30* (2013.01)

(58) Field of Classification Search
CPC .... C12P 7/54; C12P 7/065; C12P 7/08; C12P 7/18; C07C 29/1518; C12M 21/04; C12M 43/00; Y02E 50/10; Y02E 50/30

See application file for complete search history.

(56) References Cited

U.S. PATENT DOCUMENTS

2003/0211585 A1* 11/2003 Gaddy ................ C12M 21/04
435/161
2010/0197985 A1* 8/2010 Johnston ................ B01J 37/08
585/324

* cited by examiner

*Primary Examiner* — Marcia S Noble
*Assistant Examiner* — Lauren K Van Buren
(74) *Attorney, Agent, or Firm* — Frank S. Molinaro

(57) ABSTRACT

Methods and systems for the production of one or more products from a gas stream produced in a methanol production process. The method comprises converting at least a portion of a methane feedstock to a substrate comprising CO and H2. The substrate comprising CO and H2 is anaerobically fermented in a bioreactor to produce one or more alcohols. The method and system may further include process for the production of methanol processes for the production of acetic acid.

12 Claims, 3 Drawing Sheets

METHODS AND SYSTEMS FOR THE PRODUCTION OF ALCOHOLS AND/OR ACIDS

CROSS REFERENCE TO A RELATED APPLICATION

The application is a continuation of co-pending U.S. application Ser. No. 13/882,688, filed on Jul. 31, 2013, which claims the benefit of International Application No. PCT/US2011/057220, filed on Oct. 22, 2010 and of New Zealand Application No. 589003, filed on Nov. 14, 2010, the contents of which are hereby incorporated by reference.

FIELD OF THE INVENTION

This invention relates to systems and methods for improving overall carbon capture and/or improving overall efficiency in processes including microbial fermentation. In particular, the invention relates to improving carbon capture and/or improving efficiency in processes including microbial fermentation of a reformed substrate stream comprising CO and H2.

BACKGROUND OF THE INVENTION

Ethanol is rapidly becoming a major hydrogen-rich liquid transport fuel around the world. Worldwide consumption of ethanol in 2005 was an estimated 12.2 billion gallons. The global market for the fuel ethanol industry has also been predicted to grow sharply in future, due to an increased interest in ethanol in Europe, Japan, the USA, and several developing nations.

For example, in the USA, ethanol is used to produce E10, a 10% mixture of ethanol in gasoline. In E10 blends the ethanol component acts as an oxygenating agent, improving the efficiency of combustion and reducing the production of air pollutants. In Brazil, ethanol satisfies approximately 30% of the transport fuel demand, as both an oxygenating agent blended in gasoline, and as a pure fuel in its own right. Also, in Europe, environmental concerns surrounding the consequences of Green House Gas (GHG) emissions have been the stimulus for the European Union (EU) to set member nations a mandated target for the consumption of sustainable transport fuels such as biomass derived ethanol.

The vast majority of fuel ethanol is produced via traditional yeast-based fermentation processes that use crop derived carbohydrates, such as sucrose extracted from sugarcane or starch extracted from grain crops, as the main carbon source. However, the cost of these carbohydrate feedstocks is influenced by their value as human food or animal feed, while the cultivation of starch or sucrose-producing crops for ethanol production is not economically sustainable in all geographies. Therefore, it is of interest to develop technologies to convert lower cost and/or more abundant carbon resources into fuel ethanol.

CO is a major, low cost, energy-rich by-product of the incomplete combustion of organic materials such as coal or oil and oil derived products. For example, the steel industry in Australia is reported to produce and release into the atmosphere over 500,000 tonnes of CO annually. Additionally, or alternatively, CO rich gas streams (syngas) can be produced by gasification of carbonaceous materials, such as coal, petroleum and biomass. Carbonaceous materials can be converted into gas products including CO, CO2, H2 and lesser amounts of CH4 by gasification using a variety of methods, including pyrolysis, tar cracking and char gasification. Syngas can also be produced in a steam reformation process, such as the steam reformation of methane or natural gas. Methane can be converted to hydrogen and carbon monoxide and/or carbon dioxide by methane reformation in the presence of a metal catalyst. For example, steam reformation of methane occurs as follows:

$$CH_4 + H_2O \rightarrow CO + 3H_2 \quad (1)$$

$$CO + H_2O \rightarrow CO_2 + H_2 \quad (2)$$

This process accounts for a substantial portion of the hydrogen produced in the world today. Attempts to use the hydrogen produced in the above reactions in fuel cell technology have been largely unsuccessful, due to the presence of carbon monoxide, which typically poisons fuel cell catalysts. Other catalytic processes may be used to convert gases consisting primarily of CO and/or CO and hydrogen (H2) into a variety of fuels and chemicals. Micro-organisms may also be used to convert these gases into fuels and chemicals. These biological processes, although generally slower than chemical reactions, have several advantages over catalytic processes, including higher specificity, higher yields, lower energy costs and greater resistance to poisoning.

The ability of micro-organisms to grow on CO as a sole carbon source was first discovered in 1903. This was later determined to be a property of organisms that use the acetyl coenzyme A (acetyl CoA) biochemical pathway of autotrophic growth (also known as the Woods-Ljungdahl pathway and the carbon monoxide dehydrogenase I acetyl CoA synthase (CODH/ACS) pathway). A large number of anaerobic organisms including carboxydotrophic, photosynthetic, methanogenic and acetogenic organisms have been shown to metabolize CO to various end products, namely CO2, H2, methane, n-butanol, acetate and ethanol. While using CO as the sole carbon source, all such organisms produce at least two of these end products.

Anaerobic bacteria, such as those from the genus *Clostridium*, have been demonstrated to produce ethanol from CO, CO2 and H2 via the acetyl CoA biochemical pathway. For example, various strains of *Clostridium ljungdahlii* that produce ethanol from gases are described in WO00/68407, EP 117309, U.S. Pat. Nos. 5,173,429, 5,593,886, and 6,368,819, WO 98/00558 and WO 02/08438. The bacterium *Clostridium autoethanogenum* sp is also known to produce ethanol from gases (Abrini et al., Archives of Microbiology 161, pp 345-351 (1994)).

However, ethanol production by micro-organisms by fermentation of gases is typically associated with co-production of acetate and/or acetic acid. As some of the available carbon is typically converted into acetate/acetic acid rather than ethanol, the efficiency of production of ethanol using such fermentation processes may be less than desirable. Also, unless the acetate/acetic acid by-product can be used for some other purpose, it may pose a waste disposal problem. Acetate/acetic acid is converted to methane by micro-organisms and therefore has the potential to contribute to GHG emissions.

WO2007/117157 and WO2008/115080, the disclosure of which are incorporated herein by reference, describe processes that produce alcohols, particularly ethanol, by anaerobic fermentation of gases containing carbon monoxide. Acetate produced as a by-product of the fermentation process described in WO2007/117157 is converted into hydrogen gas and carbon dioxide gas, either or both of which may be used in the anaerobic fermentation process.

The fermentation of gaseous substrates comprising CO, to produce products such as acids and alcohols, typically favours acid production. Alcohol productivity can be enhanced by methods known in the art, such as methods described in WO2007/117157, WO2008/115080, WO2009/022925 and WO2009/064200, which are fully incorporated herein by reference.

U.S. Pat. No. 7,078,201 and WO 02/08438 also describe fermentation processes for producing ethanol by varying conditions (e.g. pH and redox potential) of the liquid nutrient medium in which the fermentation is performed. As disclosed in those publications, similar processes may be used to produce other alcohols, such as butanol.

Microbial fermentation of CO in the presence of H2 can lead to substantially complete carbon transfer into an alcohol. However, in the absence of sufficient H2, some of the CO is converted into alcohol, while a significant portion is converted to CO2 as shown in the following equations:

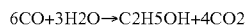

$$6CO + 3H_2O \rightarrow C_2H_5OH + 4CO_2$$

$$12H_2 + 4CO_2 \rightarrow 2C_2H_2OH + 6H_2O$$

The production of CO2 represents inefficiency in overall carbon capture and if released, also has the potential to contribute to Green House Gas emissions. Furthermore, carbon dioxide and other carbon containing compounds, such as methane, produced during a gasification process may also be released into the atmosphere if they are not consumed in an integrated fermentation reaction.

It is an object of the present invention to provide system(s) and/or method(s) that overcomes disadvantages known in the art and provides the public with new methods for the optimal production of a variety of useful products.

SUMMARY OF THE INVENTION

In accordance with a first aspect, the invention provides a method for producing products from a gas stream produced in the methanol production process, the method comprising:
1) conversion of at least a portion of the gas stream comprising methane to a substrate stream comprising CO and H2;
2) anaerobic fermentation of at least a portion of the CO and optionally H2 from step (1) to produce liquid products.

In particular embodiments of the invention, gas is converted to a substrate stream comprising CO and H2 by catalytic oxidation. In particular embodiments, at least portions of components such as H2S, CO2, O2 and/or N2 are removed from the gas prior to catalytic oxidation. Those skilled in the art will appreciate methods for removal of one or more components from a gas stream. Additionally, or alternatively, a methane component of the gas stream is enriched prior to catalytic oxidation.

In particular embodiments, the method includes passing the gas stream comprising CO and H2 to a methanol synthesis reaction vessel, wherein at least a portion of the gas is converted to methanol. In particular embodiments, at least a portion of the gas stream comprising CO and H2 is passed to a bioreactor for the production of one or more liquid products by microbial fermentation. In particular embodiments, the gas stream comprising CO and H2 is passed to the bioreactor prior to passing to the methanol synthesis reaction vessel. In another embodiment, the gas stream comprising CO and H2 is passed to the bioreactor after is has exited the methanol synthesis reaction vessel. In particular embodiments of the various preceding aspects, the anaerobic fermentation produces products including acid(s) and alcohol(s) from CO and optionally H2. In particular embodiments, the anaerobic fermentation is conducted in a bioreactor, wherein one or more microbial cultures convert CO and optionally H2 to products including acid(s) and/or alcohol(s). In certain embodiments, the product is ethanol. In particular embodiments, the acid is acetate.

In particular embodiments, the microbial culture is a culture of carboxydotrophic bacteria. In certain embodiments, the bacteria is selected from *Clostridium, Moorella* and *Carboxydothermus*. In particular embodiments, the bacterium is *Clostridium autoethanogenum*. According to various embodiments of the invention, the substrate stream and/or the blended stream provided to the fermentation will typically contain a major proportion of CO, such as at least about 20% to about 95% CO by volume, from 40% to 95% CO by volume, from 40% to 60% CO by volume, and from 45% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when significant amounts of H2 and optionally CO2 are present.

In particular embodiments of the preceding aspects, the anaerobic fermentation produces a hydrogen rich gas in addition to products. In certain embodiments, the hydrogen rich gas comprising H2 and optionally CO2 are passed into a second bioreactor. In certain embodiments anaerobic fermentation is conducted in the second bioreactor, wherein one or more microbial cultures convert H2 and CO2 to products including acid(s) and/or alcohol(s). In certain embodiments, the product is acetate.

In particular embodiments, the microbial culture of the second is a bacterium selected from *Acetobacterium* and *Moorella*. In particular embodiments, the bacterium is *Acetobacterium woodii*.

According to a second aspect, the invention provides a system for producing products by microbial fermentation, the system including:
1) a catalytic oxidation stage, wherein methane is converted to a substrate stream comprising CO and H2;
2) a methanol synthesis vessel configured to convert at least a portion of the substrate stream comprising CO and H2 to methanol;
3) means to pass the substrate stream comprising CO and H2 to a bioreactor prior to and/or after the stream is passed to the methanol synthesis vessel; and
4) a bioreactor configured to convert at least a portion of the substrate stream to products by microbial fermentation.

A gas separation stage may optionally remove at least portions of one or more components from a gas stream prior to catalytic oxidation.

In particular embodiments, the system comprises means for determining whether the substrate stream comprising CO and H2 has a desired composition. Any known means may be used for this purpose. In particular embodiments, the system further includes blending means configured to blend CO and/or H2 to the substrate stream prior to passing to the bioreactor. In particular embodiments, the system comprises means for diverting gas away from the bioreactor if the means for determining determines that the gas does not have the desired composition.

In particular embodiments of the invention, the system includes means for heating and/or cooling the various streams passed between various stages of the system. Additionally, or alternatively, the system includes means for compressing at least portions of the various streams passed between various stages of the system.

According to a third aspect, the invention provides a system for producing products, the system including:
1) a catalytic oxidation stage, wherein methane is converted to a substrate stream comprising CO and H2;
2) a methanol synthesis vessel configured to convert at least a portion of the substrate stream comprising CO and H2 to methanol means to pass the substrate stream comprising CO and H2 to a bioreactor prior to and/or after the stream is passed to the methanol synthesis vessel;
3) a first bioreactor containing a culture of one or more microorganisms, the bioreactor being configured to convert at least a portion of the substrate stream to one or more alcohol(s) by microbial fermentation;
4) a means to pass a hydrogen rich substrate stream exiting the first bioreactor of step (4) to a second bioreactor;
5) a second bioreactor containing culture of one or more microorganisms, the bioreactor configured to convert at least a portion of the substrate steam of step (5) to one or more acid(s) by microbial fermentation.

In particular embodiments the hydrogen rich substrate of step (5) further comprises carbon dioxide. In certain embodiments, the hydrogen rich substrate of step (5) is blended with carbon dioxide from an alternative source, prior to the substrate being passed to the second bioreactor of step (6).

In one embodiment the one or more alcohols of step (4) is ethanol. In one embodiment the one or more alcohols is 2,3-butanediol. In one embodiment the one or more acids of step (6) is acetic acid or acetate.

In particular embodiments the culture of the first bioreactor is a culture of carboxydotrophic bacteria. In certain embodiments, the bacteria is selected from *Clostridium*, *Moorella* and *Carboxydothermus*. In particular embodiments, the bacterium is *Clostridium autoethanogenum*.

In one embodiment the culture of the second bioreactor is a culture of one or more microorganisms selected from the group comprising *Acetobacterium, Moorella, Clostridium, Ruminococcus, Acetobacterium, Eubacterium, Butyribacterium, Oxobacter, Methanosarcina, Methanosarcina,* and *Desulfotomaculum*. In one embodiment the one or more microorganisms is *Acetobacterium woodii*. In one embodiment the one or more microorganism is *Moorella thermoaceticum*.

According to a fourth aspect, the invention provides a method for producing one or more alcohols, the method including:
1) receiving one or more products and/or by-products and/or waste products of a first process and/or one or more derivatives of said products or by-products or waste products in a bioreactor containing a culture of one or more microorganisms; and
2) fermenting the culture in the bioreactor to produce said one or more alcohols; wherein, the fist process is a process for the production of acetic acid.

In one embodiment the first process is methanol carbonylation, whereby methanol and carbon monoxide react to produce acetic acid, although other methods of acetic acid production may be used.

In one embodiment, at least a portion of the methanol and/or carbon monoxide used in the production of acetic acid according to the first process of step (1) is received from a methanol synthesis reaction.

In one embodiment, said carbon monoxide is produced as or contained in an industrial gas.

In one embodiment, at least a portion of the products of the first process is fed directly to the bioreactor. The products of the first process that are fed to the bioreactor may include any one or more of: CO, N2, CO2, CH4, methanol, acetic acid, as well as others.

In certain embodiments one or more other feedstocks are provided to the bioreactor. According to certain embodiments, said one or more other feedstocks include an industrial waste gas. In some embodiments, the one or more other feedstocks include waste streams from other processes.

Preferably the one or more feedstocks provided to the bioreactor comprise at least CO and/or H2.

Preferably, said alcohols include any one or more of ethanol or propanol, or butanol, although others are envisaged such as diols, particularly 2,3-butanediol.

The fermentation may additionally or alternatively produce any one or more of: butyrate, propionate, caproate, propylene, butadiene, iso-butylene, or ethylene.

Preferably, the biomass product is used to produce supplemental heat to drive one or more reactions, preferably at least one of those defined herein.

Preferably, the method includes providing one or more products and/or by-products and/or waste products of the fermentation and/or one or more derivatives of said products or by-products or waste products for use in said first process.

According to a fifth aspect, the invention provides a system for the production of one or more products, the system including:
1) a catalytic oxidation stage, wherein methane is converted to a substrate stream comprising CO and H2;
2) a methanol synthesis vessel configured to convert at least a portion of the substrate stream comprising CO and H2 to methanol;
3) means to pass at least a portion of the substrate stream comprising CO and/or H2 of (2) to the methanol synthesis vessel, and means to pass at least a portion of the substrate stream comprising CO and/or H2 of (2) to a bioreactor prior to and/or after the stream is passed to the methanol synthesis vessel;
4) a first bioreactor containing a culture of one or more microorganisms, the bioreactor being configured to convert at least a portion of the substrate stream to one or more alcohol(s) by microbial fermentation;
5) a methanol carbonylation vessel configured to convert methanol and CO to one or more products and/or by-products and/or waste products, wherein the methanol carbonylation vessel is configured to receive at least a portion of the methanol and/or CO from the methanol synthesis vessel;
6) means to pass at least a portion of the methanol and/or CO of step (2) from the methanol synthesis vessel to the methanol carbonylation vessel; and
7) means to pass at least a portion of the one or more products and/or byproducts and/or waste products of (5) to the bioreactor of 4 for use as co-substrate(s) in the microbial fermentation.

In particular embodiments, the system further comprises a second bioreactor containing a culture of one or more microorganisms, the bioreactor configured to convert at least a portion of a hydrogen rich substrate steam to one or more acid(s) by microbial fermentation; and a means to pass a hydrogen rich substrate stream exiting the first bioreactor of step (4) to a second bioreactor; wherein the hydrogen rich substrate stream is a by-product of the fermentation reaction of step (4).

In certain embodiments, the one or more product(s) of step (5) is acetic acid. In certain embodiments the acetic acid is produced by methanol carbonylation, whereby methanol and carbon monoxide react to produce acetic acid, although other methods of acetic acid production may be used.

In one embodiment, at least a portion of the methanol and/or carbon monoxide used in the production of acetic acid according step (5) is received from a methanol synthesis reaction.

In one embodiment at least a portion of the methanol and/or carbon monoxide used in step (5) is received from other sources.

In one embodiment, said carbon monoxide is produced as or contained in an industrial gas.

In one embodiment, at least a portion of the products of the methanol carbonylation reaction in step (5) is fed directly to the bioreactor. The products of the first process that are fed to the bioreactor may include any one or more of: CO, N2, CO2, CH4, methanol, acetic acid, as well as others.

In certain embodiments one or more other feedstocks are provided to the bioreactor. According to certain embodiments, said one or more other feedstocks include an industrial waste gas. In some embodiments, the one or more other feedstocks include waste streams from other processes.

Preferably the one or more feedstocks provided to the bioreactor comprise at least CO and/or H2.

Preferably, said alcohols include any one or more of ethanol or propanol, or butanol, although others are envisaged such as diols, particularly 2,3-butanediol.

The fermentation may additionally or alternatively produce any one or more of: butyrate, propionate, caproate, propylene, butadiene, iso-butylene, or ethylene.

The methods and systems of the preceding aspect have significant potential for reducing greenhouse gas emissions. According to conventional methanol carbonylation processes, CO is a waste product which may be flared or burnt after acetic acid has been separated. Of the waste stream of methanol carbonylation, around 65-70% may comprise CO. By tying conventional acetic acid production methods to one or more fermentation reactions, waste products of the acetic acid production process can be used to produce valuable and/or useful products.

Although the invention is broadly as defined above, it is not limited thereto and also includes embodiments of which the following description provides examples.

Figure 1:
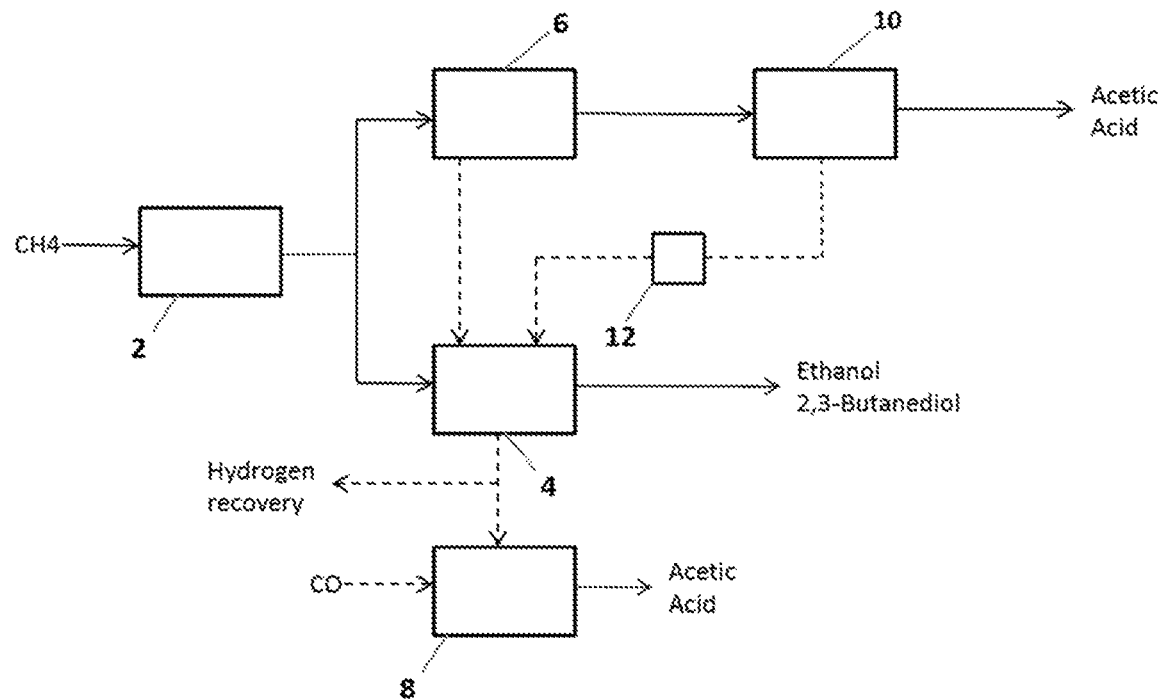
FIG. 1 shows a system and method according to the fifth aspect of the invention.

Note that the blocks of FIGS. 1 to 5 represent both method steps and components/modules of the physical system.

DETAILED DESCRIPTION OF THE INVENTION

Definitions

Unless otherwise defined, the following terms as used throughout this specification are defined as follows:

The terms "carbon capture" and "overall carbon capture" refer to the efficiency of conversion of a carbon source, such as a feedstock, into products. For example, the amount of carbon in a woody biomass feedstock converted into useful products, such as alcohol.

The term "syngas" refers to a gas mixture that contains at least a portion of carbon monoxide and hydrogen produced by gasification and/or reformation of a carbonaceous feedstock.

The term "substrate comprising carbon monoxide" and like terms should be understood to include any substrate in which carbon monoxide is available to one or more strains of bacteria for growth and/or fermentation, for example.

"Gaseous substrates comprising carbon monoxide" include any gas which contains carbon monoxide. The gaseous substrate will typically contain a significant proportion of CO, preferably at least about 5% to about 95% CO by volume.

The term "bioreactor" includes a fermentation device consisting of one or more vessels and/or towers or piping arrangements, which includes the continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR), or other vessel or other device suitable for gas-liquid contact.

In the context of fermentation products, the term "acid" as used herein includes both carboxylic acids and the associated carboxylate anion, such as the mixture of free acetic acid and acetate present in a fermentation broth as described herein. The ratio of molecular acid to carboxylate in the fermentation broth is dependent upon the pH of the system. The term "acetate" includes both acetate salt alone and a mixture of molecular or free acetic acid and acetate salt, such as the mixture of acetate salt and free acetic acid present in a fermentation broth as may be described herein. The ratio of molecular acetic acid to acetate in the fermentation broth is dependent upon the pH of the system.

The term "desired composition" is used to refer to the desired level and types of components in a substance, such as, for example, of a gas stream. More particularly, a gas is considered to have a "desired composition" if it contains a particular component (e.g. CO and/or H2) and/or contains a particular component at a particular level and/or does not contain a particular component (e.g. a contaminant harmful to the micro-organisms) and/or does not contain a particular component at a particular level. More than one component may be considered when determining whether a gas stream has a desired composition.

The term "stream" is used to refer to a flow of material into, through and away from one or more stages of a process, for example, the material that is fed to a bioreactor and/or an optional CO2 remover. The composition of the stream may vary as it passes through particular stages. For example, as a stream passes through the bioreactor, the CO content of the stream may decrease, while the CO2¬ content may increase. Similarly, as the stream passes through the CO2 remover stage, the CO2 content will decrease.

Unless the context requires otherwise, the phrases "fermenting", "fermentation process" or "fermentation reaction" and the like, as used herein, are intended to encompass both the growth phase and product biosynthesis phase of the process.

"Fermentation broth" is defined as the culture medium in which fermentation occurs.

The terms "increasing the efficiency", "increased efficiency" and the like, when used in relation to a fermentation process, include, but are not limited to, increasing one or more of: the rate of growth of micro-organisms in the fermentation, the volume or mass of desired product (such as alcohols) produced per volume or mass of substrate (such as carbon monoxide) consumed, the rate of production or level of production of the desired product, and the relative proportion of the desired product produced compared with other by-products of the fermentation, and further may reflect the value (which may be positive or negative) of any by-products generated during the process.

The term "process for producing acetic acid", the like or corresponding apparatus relate to any process or apparatus that may be used to produce acetic acid, including but not limited to methanol carbonylation While certain embodiments of the invention, namely those that include the production of ethanol by anaerobic fermentation using CO and H2 as the primary substrate, are readily recognized as being valuable improvements to technology of great interest today, it should be appreciated that the invention is applicable to production of alternative products such as other alcohols and the use of alternative substrates, particularly gaseous substrates, as will be known by persons of ordinary skill in the art to which the invention relates upon consideration of the instant disclosure. For example, gaseous substrates containing carbon dioxide and hydrogen may be used in particular embodiments of the invention. Further, the invention may be applicable to fermentations to produce acetate, butyrate, propionate, caproate, ethanol, propanol, and butanol, and hydrogen. By way of example, these products may be produced by fermentation using microbes from the genus *Moorella, Clostridia, Ruminococcus, Acetobacterium, Eubacterium, Butyribacterium, Oxobacter, Methanosarcina, Methanosarcina,* and *Desulfotomaculum.*

Methanol Production

During the production of methanol, a gas stream comprising CO is reduced at high temperature and pressure using H2 over a metal catalyst in a gas phase methanol synthesis reaction vessel. The reduction of CO is highly exothermic, and excess heat is typically removed from the process by recycling the gas stream comprising CO through the reaction vessel. It has been surprisingly recognised that at least a portion of the gas stream comprising CO and H2 used in the methanol production process can be converted to ethanol or other liquid products by microbial fermentation. In particular embodiments, the invention includes diverting at least a portion of the gas stream comprising CO and H2 to a bioreactor comprising one or more microorganisms, to produce ethanol and/or other liquid products. In a particular embodiment, the gas stream comprising CO and H2 is diverted to the bioreactor prior to passing to the methanol synthesis reaction vessel. In another embodiment, the gas stream comprising CO H2 is passed to the bioreactor after passing out of the methanol synthesis reaction vessel.

A common method of methanol production includes the reduction of CO using H2 in the presence of a metal catalyst. The reduction is typically conducted at elevated temperature and pressure in a gas phase reactor. Typically, the reduction is not quantitative and a stream comprising CO and optionally H2 will exit the gas phase reactor, wherein the exiting gas stream can be recycled or vented. The process is highly exothermic, and at least a portion of the exotherm can be removed from the process by recycling the gas stream through the methanol synthesis reactor. Additionally, or alternatively, at least a portion of the exotherm can be removed by externally cooling the methanol synthesis reactor, such as water cooling. The CO used in the reduction is typically a component in a syngas stream derived from the reformation of methane. In accordance with the methods of the invention, methane is converted to a reformed substrate stream comprising CO and H2 by catalytic oxidation. In particular embodiments, methane is converted to CO and H2 in the presence of a metal catalyst at elevated temperature. The most common catalytic oxidation process is steam reforming, wherein methane and steam are reformed to CO and H2 at 700-1100° C. in the presence of a nickel catalyst. The stoichiometry of the conversion is as follows:

$$CH4+H2O \rightarrow CO+3H2$$

Additionally, or alternatively, autothermal reforming can be used to partially oxidise methane in the presence of oxygen at elevated temperature and pressure as follows:

$$2CH4+O2+CO2 \rightarrow 3H2+3CO+H2O$$

$$2CH4+O2+H2O \rightarrow 5H2+2CO$$

Dry reforming takes advantage of the significant portion of CO2 present in biogas to produce carbon monoxide and hydrogen as follows:

$$CH4+CO2 \rightarrow 2CO+2H2$$

In accordance with the methods of the invention, the CO and H2 produced in the catalytic oxidation are used in the production of methanol by passing the gas stream comprising CO to a methanol synthesis reactor. In accordance with particular embodiments, at least a portion of the gas stream comprising CO is passed to a bioreactor for conversion to liquid products by microbial fermentation. In particular embodiments, at least a portion of the gas stream comprising CO exiting the methanol synthesis reactor is passed to a bioreactor for conversion to liquid products by microbial fermentation.

The gas stream exiting the methanol synthesis reaction vessel will typically have an enriched H2 component relative to CO. Thus, in particular embodiments, the H2 enriched gas stream can be combined with CO2 and passed to a bioreactor for conversion to acid products, such as acetate. In particular embodiments, the CO2 is included in a gas stream.

An advantage of particular embodiments of the invention is the increase in efficiency resulting from decreased recycling of a stream comprising CO and H2 through the methanol synthesis reaction vessel. In particular embodiments, there is less load on a recycle compressor. In another embodiment, the process reduces the build-up of inert components in the gas stream that is recycled.

Blending of Streams

As noted previously, it may be desirable to blend a reformed substrate stream comprising CO and H2 with one or more further streams in order to improve efficiency, alcohol production and/or overall carbon capture of the fermentation reaction. Without wishing to be bound by theory, in some embodiments of the present invention, carboxydotrophic bacteria convert CO to ethanol according to the following:

However, in the presence of H2, the overall conversion can be as follows:

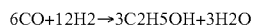

Accordingly, streams with high CO content can be blended with reformed substrate streams comprising CO and H2 to increase the CO:H2 ratio to optimise fermentation efficiency. By way of example, industrial waste streams, such as off-gas from a steel mill have a high CO content but include minimal or no H2. As such, it can be desirable to blend one or more streams comprising CO and H2 with the waste stream comprising CO, prior to providing the blended substrate stream to the fermenter. The overall efficiency, alcohol productivity and/or overall carbon capture of the fermentation will be dependent on the stoichiometry of the CO and H2 in the blended stream. However, in particular embodiments the blended stream may substantially comprise CO and H2 in the following molar ratios: 20:1, 10:1, 5:1, 3:1, 2:1, 1:1 or 1:2.

In addition, it may be desirable to provide CO and H2 in particular ratios at different stages of the fermentation. For example, substrate streams with a relatively high H2 content (such as 1:2 CO:H2) may be provided to the fermentation stage during start up and/or phases of rapid microbial growth. However, when the growth phase slows, such that the culture is maintained at a substantially steady microbial density, the CO content may be increased (such as at least 1:1 or 2:1 or higher, wherein the H2 concentration may be greater or equal to zero).

Blending of streams may also have further advantages, particularly in instances where a waste stream comprising CO is intermittent in nature. For example, an intermittent waste stream comprising CO may be blended with a substantially continuous reformed substrate stream comprising CO and H2 and provided to the fermenter. In particular embodiments of the invention, the composition and flow rate of the substantially continuous blended stream may be varied in accordance with the intermittent stream in order to maintain provision of a substrate stream of substantially continuous composition and flow rate to the fermenter.

Blending of two or more streams to achieve a desirable composition may involve varying flow rates of all streams, or one or more of the streams may be maintained constant while other stream(s) are varied in order to 'trim' or optimise the blended stream to the desired composition. For streams that are processed continuously, little or no further treatment (such as buffering) may be necessary and the stream can be provided to the fermenter directly. However, it may be necessary to provide buffer storage for streams where one or more is available intermittently, and/or where streams are available continuously, but are used and/or produced at variable rates.

Those skilled in the art will appreciate it will be necessary to monitor the composition and flow rates of the streams prior to blending. Control of the composition of the blended stream can be achieved by varying the proportions of the constituent streams to achieve a target or desirable composition. For example, a base load gas may be predominantly CO and H2 of a particular ratio, and a secondary gas comprising a high concentration of CO may be blended to achieve a specified H2:CO ratio. The composition and flow rate of the blended stream can be monitored by any means known in the art. The flow rate of the blended stream can be controlled independently of the blending operation; however, the rates at which the individual constituent streams can be drawn must be controlled within limits. For example, a stream produced intermittently, drawn continuously from buffer storage, must be drawn at a rate such that buffer storage capacity is neither depleted nor filled to capacity.

At the point of blending, the individual constituent gases will enter a mixing chamber, which will typically be a small vessel, or a section of pipe. In such cases, the vessel or pipe may be provided with static mixing devices, such as baffles, arranged to promote turbulence and rapid homogenisation of the individual components.

Buffer storage of the blended stream can also be provided if necessary, in order to maintain provision of a substantially continuous substrate stream to the bioreactor.

A processor adapted to monitor the composition and flow rates of the constituent streams and control the blending of the streams in appropriate proportions, to achieve the required or desirable blend may optionally be incorporated into the system. For example, particular components may be provided in an as required or an as available manner in order to optimise the efficiency of alcohol productivity and/or overall carbon capture.

It may not be possible or cost effective to provide CO and H2 at a particular ratio all the time. As such, a system adapted to blend two or more streams as described above may be adapted to optimise the ratio with the available resources. For example, in instances where an inadequate supply of H2 is available, the system may include means to divert excess CO away from the system in order to provide an optimised stream and achieve improved efficiency in alcohol production and/or overall carbon capture. In certain embodiments of the invention, the system is adapted to continuously monitor the flow rates and compositions of at least two streams and combine them to produce a single blended substrate stream of optimal composition and means for passing the optimised substrate stream to the fermenter. In particular embodiments employing carboxydotrophic microbes to produce alcohol, the optimum composition of substrate stream comprising at least 1% H2 and up to about 1:2 CO:H2.

By way of non-limiting example, particular embodiments of the invention involve the utilisation of converter gas from the decarburisation of steel as a source of CO. Typically, such streams contain little or no H2, therefore it may be desirable to combine the stream comprising CO with a reformed substrate stream comprising CO and H2 in order to achieve a more desirable CO:H2 ratio.

Additionally, or alternatively, a gasifier may be provided to produce CO and H2 from a variety of sources. The stream produced by the gasifier may be blended with a reformed substrate stream comprising CO and H2 to achieve a desirable composition. Those skilled in the art will appreciate that gasifier conditions can be controlled to achieve a particular CO:H2 ratio. Furthermore, the gasifier may be ramped up and down to increase and decrease the flow rate of the reformed substrate stream comprising CO and H2 produced by the gasifier. Accordingly, a stream from a gasifier may be blended with a substrate stream comprising CO and H2 to optimise the CO:H2 ratio in order to increase alcohol productivity and/or overall carbon capture. Furthermore, the gasifier may be ramped up and down to provide a stream of varying flow and/or composition that may be blended with an intermittent stream comprising CO and H2 to achieve a substantially continuous stream of desirable composition.

Acetic Acid Production

Aspects of the present invention include processes for producing acetic acid. A number of processes for producing acetic acid are known. Processes for producing acetic acid include those described below. A skilled person would understand that processes for producing acetic acid are not limited to those processes described herein and may include other known methods.

Methanol Carbonylation

In this process, methanol and carbon monoxide react to produce acetic acid according to the equation:

CH3OH+CO→CH3COOH

This is a simplification of the actual process which generates and consumes iodomethane as an intermediate, usually in the presence of a metal complex catalyst. The process is more fully set out below:

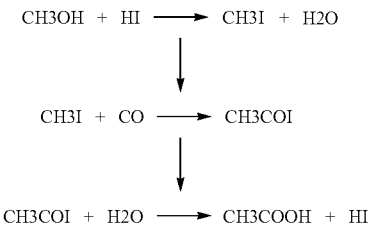

Various catalysts may be used in the process. More recently, the Cativa catalyst ([Ir(CO)2I2]⁻), promoted by ruthenium, has been used. This catalyst provides greener and more efficient processing than earlier catalysts.

Acetaldehyde Oxidation

Acetaldehyde may be produced by oxidation of butane or light naphtha, or by hydration of ethylene. When butane or light naphtha is heated with air in the presence of various metal ions (e.g. manganese, cobalt, chromium), peroxides form and then decompose to produce acetic acid according to:

2C4H10+5O2→4CH3COOH+2H2O

To improve the reaction, elevated temperatures and pressures may be used (e.g. 150° C. and 55 atm).

As an alternative to butane oxidation, acetaldehyde can be oxidised by oxygen in air under similar conditions and using similar catalysts, according to:

2CH3CHO+O2→2CH3COOH

Ethylene Oxidation

Acetaldehyde may alternatively be produced from ethylene using the Wacker process and then oxidised as described previously. A single stage conversion of ethylene to acetic acid has also been commercialised, whereby ethylene is oxidised in the presence of a palladium metal catalyst supported on a heteropoly acid such as tungstosilicic acid.

Oxidative Fermentation

Acetic acid in the form of vinegar has historically been made by acetic acid bacteria of the genus Acetobacter. Given sufficient oxygen, these bacteria can produce vinegar from a variety of foodstuffs such as cider, wine, or fermented grain, malt, rice or potato. The reaction is:

C2H5OH+O2→CH3COOH+H2O

Nowadays, most vinegar is made in submerged tank culture, fermenting alcohol to vinegar in a continuously stirred tank with oxygen supplied by bubbling air through the fermentation broth.

Anaerobic Fermentation

As described hereinbefore, anaerobic bacteria such as Clostridium can convert sugars to acetic acid according to:

C6H12O6→3CH3COOH

These acetogenic bacteria can also produce acetic acid from one-carbon compounds, including methanol, carbon monoxide or a mixture of carbon dioxide and hydrogen according to:

2CO2+4H2→CH3COOH+2H2O

The ability of *Clostridium* to use sugars or other feedstocks to directly produce acetic acid means that these bacteria could produce acetic acid more efficiently than ethanol oxidisers such as *Acetobacter*. However, *Clostridium* bacteria are generally less acid-tolerant than *Acetobacter*, historically limiting the resultant concentration of acid to a few percent, compared to up to about 20% when using *Acetobacter*. Consequently, the use of Acetobacter is generally preferred due to the reduced costs of harvesting the acetic acid produced In view of the volumes of acetic acid that are produced, it will be appreciated that small changes in process efficiency can be of value. Further, the ability to adapt to changing conditions during the production and/or use of acetic acid is desirable.

Fermentation Reaction

Particular embodiments of the invention include the fermentation of a syngas substrate stream to produce products including alcohol(s) and optionally acid(s). Processes for the production of ethanol and other alcohols from gaseous substrates are known. Exemplary processes include those described for example in WO2007/117157, WO2008/115080, U.S. Pat. Nos. 6,340,581, 6,136,577, 5,593,886, 5,807,722 and 5,821,111, each of which is incorporated herein by reference.

A number of anaerobic bacteria are known to be capable of carrying out the fermentation of CO to alcohols, including n-butanol and ethanol, and acetic acid, and are suitable for use in the process of the present invention. Examples of such bacteria that are suitable for use in the invention include those of the genus Clostridium, such as strains of Clostridium ljungdahlii, including those described in WO 00/68407, EP 117309, U.S. Pat. Nos. 5,173,429, 5,593,886, and 6,368,819, WO 98/00558 and WO 02/08438, *Clostridium carboxydivorans* (Liou et al., International Journal of Systematic and Evolutionary Microbiology 33: pp 2085-2091) and Clostridium autoethanogenum (Abrini et al, Archives of Microbiology 161: pp 345-351). Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Clostridium autoethanogenum*. In one embodiment, the *Clostridium autoethanogenum* is a *Clostridium autoethanogenum* having the identifying characteristics of the strain deposited at the German Resource Centre for Biological Material (DSMZ) under the identifying deposit number 19630. In one embodiment, the *Clostridium autoethanogenum* is a *Clostridium autoethanogenum* having the identifying characteristics of the strain deposited at the German Resource Centre for Biological Material (DSMZ) under the identifying deposit number 23693. In another embodiment, the *Clostridium autoethanogenum* is a *Clostridium autoethanogenum* having the identifying characteristics of DSMZ deposit number DSMZ 10061. Examples of fermentation of a substrate comprising CO to produce products including alcohols by Clostridium autoethanogenum are provided in WO2007/117157, WO2008/115080, WO2009/022925, WO2009/058028, WO2009/064200, WO2009/064201, WO2009/113878 and WO2009/151342 all of which are incorporated herein by reference.

Culturing of the bacteria used in the methods of the invention may be conducted using any number of processes known in the art for culturing and fermenting substrates using anaerobic bacteria. Exemplary techniques are provided in the "Examples" section below. By way of further example, those processes generally described in the following articles using gaseous substrates for fermentation may be utilised: (i) K. T. Klasson, et al. (1991). Bioreactors for synthesis gas fermentations resources. Conservation and Recycling, 5; 145-165; (ii) K. T. Klasson, et al. (1991). Bioreactor design for synthesis gas fermentations. Fuel. 70. 605-614; (iii) K. T. Klasson, et al. (1992). Bioconversion of synthesis gas into liquid or gaseous fuels. Enzyme and Microbial Technology. 14; 602-608; (iv) J. L. Vega, et al. (1989). Study of Gaseous Substrate Fermentation: Carbon Monoxide Conversion to Acetate. 2. Continuous Culture. Biotech. Bioeng. 34. 6. 785-793; (vi) J. L. Vega, et al. (1989). Study of gaseous substrate fermentations: Carbon monoxide conversion to acetate. 1. Batch culture. Biotechnology and Bioengineering. 34. 6. 774-784; (vii) J. L. Vega, et al. (1990). Design of Bioreactors for Coal Synthesis Gas Fermentations. Resources, Conservation and Recycling. 3. 149-160; all of which are incorporated herein by reference.

The fermentation may be carried out in any suitable bioreactor configured for gas/liquid contact wherein the substrate can be contacted with one or more microorganisms, such as a continuous stirred tank reactor (CSTR), an immobilised cell reactor, a gas-lift reactor, a bubble column reactor (BCR), a membrane reactor, such as a Hollow Fibre Membrane Bioreactor (HFMBR) or a trickle bed reactor (TBR), monolith bioreactor or loop reactors. Also, in some embodiments of the invention, the bioreactor may comprise a first, growth reactor in which the micro-organisms are cultured, and a second, fermentation reactor, to which fermentation broth from the growth reactor is fed and in which most of the fermentation product (e.g. ethanol and acetate) is produced.

According to various embodiments of the invention, the carbon source for the fermentation reaction is syngas derived from gasification. The syngas substrate will typically contain a major proportion of CO, such as at least about 15% to about 75% CO by volume, from 20% to 70% CO by volume, from 20% to 65% CO by volume, from 20% to 60% CO by volume, and from 20% to 55% CO by volume. In particular embodiments, the substrate comprises about 25%, or about 30%, or about 35%, or about 40%, or about 45%, or about 50% CO, or about 55% CO, or about 60% CO by volume. Substrates having lower concentrations of CO, such as 6%, may also be appropriate, particularly when H2 and CO2 are also present. In particular embodiments, the presence of hydrogen results in an improved overall efficiency of alcohol production. The gaseous substrate may also contain some CO2 for example, such as about 1% to about 80% CO2 by volume, or 1% to about 30% CO2 by volume.

In accordance with particular embodiments of the invention, the CO content and/or the H2 content of the reformed substrate stream can be enriched prior to passing the stream to the bioreactor. For example, hydrogen can be enriched using technologies well known in the art, such as pressure swing adsorption, cryogenic separation and membrane separation. Similarly, CO can be enriched using technologies well known in the art, such as copper-ammonium scrubbing, cryogenic separation, COSORB™ technology (absorption into cuprous aluminium dichloride in toluene), vacuum swing adsorption and membrane separation. Other methods used in gas separation and enrichment are detailed in PCT/NZ2008/000275, which is fully incorporated herein by reference.

Typically, the carbon monoxide will be added to the fermentation reaction in a gaseous state. However, the methods of the invention are not limited to addition of the substrate in this state. For example, the carbon monoxide can be provided in a liquid. For example, a liquid may be saturated with a carbon monoxide containing gas and that liquid added to the bioreactor. This may be achieved using standard methodology. By way of example a microbubble dispersion generator (Hensirisak et. al. Scale-up of microbubble dispersion generator for aerobic fermentation; Applied Biochemistry and Biotechnology Volume 101, Number 3/October 2002) could be used for this purpose.

It will be appreciated that for growth of the bacteria and CO-to-alcohol fermentation to occur, in addition to the CO-containing substrate gas, a suitable liquid nutrient medium will need to be fed to the bioreactor. A nutrient medium will contain vitamins and minerals sufficient to permit growth of the micro-organism used. Anaerobic media suitable for the fermentation of ethanol using CO as the sole carbon source are known in the art. For example, suitable media are described in U.S. Pat. Nos. 5,173,429 and 5,593,886 and WO 02/08438, WO2007/117157, WO2008/115080, WO2009/022925, WO2009/058028, WO2009/064200, WO2009/064201, WO2009/113878 and WO2009/151342 referred to above. The present invention provides a novel media which has increased efficacy in supporting growth of the micro-organisms and/or alcohol production in the fermentation process. This media will be described in more detail hereinafter.

The fermentation should desirably be carried out under appropriate conditions for the desired fermentation to occur (e.g. CO-to-ethanol). Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition. Suitable conditions are described in WO02/08438, WO2007/117157, WO2008/115080, WO2009/022925, WO2009/058028, WO2009/064200, WO2009/064201, WO2009/113878 and WO2009/151342 all of which are incorporated herein by reference.

The optimum reaction conditions will depend partly on the particular micro-organism used. However, in general, it is preferred that the fermentation be performed at pressure higher than ambient pressure. Operating at increased pressures allows a significant increase in the rate of CO transfer from the gas phase to the liquid phase where it can be taken up by the micro-organism as a carbon source for the production of ethanol. This in turn means that the retention time (defined as the liquid volume in the bioreactor divided by the input gas flow rate) can be reduced when bioreactors are maintained at elevated pressure rather than atmospheric pressure.

The benefits of conducting a gas-to-ethanol fermentation at elevated pressures have also been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO and H2 containing gaseous substrate is such as to ensure that the concentration of CO in the liquid phase does not become limiting. This is because a consequence of CO-limited conditions may be that the ethanol product is consumed by the culture.

CO2 and H2 Fermentation

A number of anaerobic bacteria are known to be capable of carrying out the fermentation of CO2 and H2 to alcohols, including ethanol, and acetic acid, and are suitable for use in the process of the present invention. Acetogens have the ability to convert gaseous substrates such as H2, CO2 and CO into products including acetic acid, ethanol and other fermentation products by the Wood-Ljungdahl pathway. Examples of such bacteria that are suitable for use in the invention include those of the genus *Acetobacterium*, such as strains of *Acetobacterium woodii* ((Demler, M., Weuster-Botz, "Reaction Engineering Analysis of Hydrogenotrophic Production of Acetic Acid by Acetobacterum Woodii", Biotechnology and Bioengineering, Vol. 108, No. 2, February 2011) and.

*Acetobacterium woodii* has been shown to produce acetate by fermentation of gaseous substrates comprising CO2 and H2. Buschhom et al. demonstrated the ability of *A woodii* to produce ethanol in a glucose fermentation with a phosphate limitation.

Other suitable bacteria include those of the genus *Moorella*, including *Moorella* sp HUC22-1, (Sakai et al, Biotechnology Letters 29: pp 1607-1612), and those of the genus *Carboxydothermus* (Svetlichny, V. A., Sokolova, T. G. et al (1991), Systematic and Applied Microbiology 14: 254-260). Further examples include *Morella thermoacetica, Moorella thermoautotrophica, Ruminococcus productus, Acetobacterium woodii, Eubacterium limosum, Butyribacterium methylotrophicum, Oxobacter pfennigii, Methanosarcina barkeri, Methanosarcina acetivorans, Desulfotomaculum kuznetsovii* (Simpa et. al. Critical Reviews in Biotechnology, 2006 Vol. 26. Pp41-65). In addition, it should be understood that other acetogenic anaerobic bacteria may be applicable to the present invention as would be understood by a person of skill in the art. It will also be appreciated that the invention may be applied to a mixed culture of two or more bacteria.

One exemplary micro-organism suitable for use in the present invention is *Acetobacterium woodii* having the identifying characteristics of the strain deposited at the German Resource Centre for Biological Material (DSMZ) under the identifying deposit number DSM 1030.

CO2 and H2 Containing Substrate

Preferably the carbon source for the fermentation can be a gaseous substrate comprising carbon dioxide in combination with hydrogen. Similarly, the gaseous substrate may be a CO22 and H2 containing waste gas obtained as a by-product of an industrial process, or from some other source. The largest source of CO2 emissions globally is from the combustion of fossil fuels such as coal, oil and gas in power plants, industrial facilities and other sources.

The gaseous substrate may be a CO2 and H2-containing waste gas obtained as a by-product of an industrial process, or from some another source such as from automobile exhaust fumes. In certain embodiments, the industrial process is selected from the group consisting of hydrogen manufacture, ammonia manufacture, combustion of fuels, gasification of coal, and the production of limestone and cement. The gaseous substrate may be the result of blending one or more gaseous substrates to provide a blended stream. It would be understood to a skilled person that waste gas streams rich in H2 or rich in CO2 are more abundant that waste gas streams rich in both H2 and CO2. A skilled person would understand that blending one or more gas streams comprising one of the desired components of CO2 and H2 would fall within the scope of the present invention.

Hydrogen rich gas streams are produced by a variety of processes including steam reformation of hydrocarbons, and in particular steam reformation of natural gas. The partial oxidation of coal or hydrocarbons is also a source of hydrogen rich gas. Other sources of hydrogen rich gas include the electrolysis of water, by-products from electrolytic cells used to produce chlorine and from various refinery and chemical streams.

Gas streams typically rich in Carbon dioxide include exhaust gasses from combustion of a hydrocarbon, such as natural gas or oil. Carbon dioxide is also produced as a by-product from the production of ammonia, lime or phosphate and from natural carbon dioxide wells.

Product Recovery

The products of the fermentation reaction can be recovered using known methods. Exemplary methods include those described in WO2007/117157, WO2008/115080, WO2009/022925, U.S. Pat. Nos. 6,340,581, 6,136,577, 5,593,886, 5,807,722 and 5,821,111. However, briefly and by way of example only ethanol may be recovered from the fermentation broth by methods such as fractional distillation or evaporation, and extractive fermentation.

Distillation of ethanol from a fermentation broth yields an azeotropic mixture of ethanol and water (i.e., 95% ethanol and 5% water). Anhydrous ethanol can subsequently be obtained through the use of molecular sieve ethanol dehydration technology, which is also well known in the art.

Extractive fermentation procedures involve the use of a water-miscible solvent that presents a low toxicity risk to the fermentation organism, to recover the ethanol from the dilute fermentation broth. For example, oleyl alcohol is a solvent that may be used in this type of extraction process. Oleyl alcohol is continuously introduced into a fermenter, whereupon this solvent rises forming a layer at the top of the fermenter which is continuously extracted and fed through a centrifuge. Water and cells are then readily separated from the oleyl alcohol and returned to the fermenter while the ethanol-laden solvent is fed into a flash vaporization unit.

Most of the ethanol is vaporized and condensed while the oleyl alcohol is non-volatile and is recovered for re-use in the fermentation.

Acetate, which is produced as by-product in the fermentation reaction, may also be recovered from the fermentation broth using methods known in the art.

For example, an adsorption system involving an activated charcoal filter may be used. In this case, it is preferred that microbial cells are first removed from the fermentation broth using a suitable separation unit. Numerous filtration-based methods of generating a cell free fermentation broth for product recovery are known in the art. The cell free ethanol—and acetate—containing permeate is then passed through a column containing activated charcoal to adsorb the acetate. Acetate in the acid form (acetic acid) rather than the salt (acetate) form is more readily adsorbed by activated charcoal. It is therefore preferred that the pH of the fermentation broth is reduced to less than about 3 before it is passed through the activated charcoal column, to convert the majority of the acetate to the acetic acid form.

Acetic acid adsorbed to the activated charcoal may be recovered by elution using methods known in the art. For example, ethanol may be used to elute the bound acetate. In certain embodiments, ethanol produced by the fermentation process itself may be used to elute the acetate. Because the boiling point of ethanol is 78.8° C. and that of acetic acid is 107° C., ethanol and acetate can readily be separated from each other using a volatility-based method such as distillation.

Other methods for recovering acetate from a fermentation broth are also known in the art and may be used in the processes of the present invention. For example, U.S. Pat. Nos. 6,368,819 and 6,753,170 describe a solvent and cosolvent system that can be used for extraction of acetic acid from fermentation broths. As with the example of the oleyl alcohol-based system described for the extractive fermentation of ethanol, the systems described in U.S. Pat. Nos. 6,368,819 and 6,753,170 describe a water immiscible solvent/co-solvent that can be mixed with the fermentation broth in either the presence or absence of the fermented micro-organisms in order to extract the acetic acid product. The solvent/co-solvent containing the acetic acid product is then separated from the broth by distillation. A second distillation step may then be used to purify the acetic acid from the solvent/co-solvent system.

The products of the fermentation reaction (for example ethanol and acetate) may be recovered from the fermentation broth by continuously removing a portion of the broth from the fermentation bioreactor, separating microbial cells from the broth (conveniently by filtration), and recovering one or more product from the broth simultaneously or sequentially. In the case of ethanol, it may be conveniently recovered by distillation, and acetate may be recovered by adsorption on activated charcoal, using the methods described above. The separated microbial cells are preferably returned to the fermentation bioreactor. The cell free permeate remaining after the ethanol and acetate have been removed is also preferably returned to the fermentation bioreactor. Additional nutrients (such as B vitamins) may be added to the cell free permeate to replenish the nutrient medium before it is returned to the bioreactor. Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

General

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the biogas and reformed and/or blended substrate streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. For example, particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of CO or high levels of O2 that may be detrimental to a fermentation reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used.

Various embodiments of the systems of the invention are described in the accompanying Figures.

The alternative embodiments described in FIGS. 1 to 5 comprise features in common with one another and the same reference numbers have been used to denote the same or similar features in the various figures. Only the new features (relative to the preceding Figures) are described, and so the Figures should be considered in conjunction with the description of FIG. 1.

As shown in FIG. 1, one embodiment of the invention provides a system and method for the production of one or more products, the system including:

a) a catalytic oxidation stage 2, wherein methane is converted to a substrate stream comprising CO and H2;

b) a methanol synthesis vessel 6 configured to convert at least a portion of the substrate stream comprising CO and H2 to methanol;

c) means to pass at least a portion of the substrate stream comprising CO and/or H2 of (a) to the methanol synthesis vessel 6, and means to pass at least a portion of the substrate stream comprising CO and/or H2 of (a)to a bioreactor 4 prior to and/or after the stream is passed to the methanol synthesis vessel 6;

d) a first bioreactor 4 containing a culture of one or more microorganisms, the bioreactor 4 being configured to convert at least a portion of the substrate stream to one or more alcohol(s) by microbial fermentation;

e) a methanol carbonylation vessel 10 configured to convert methanol and CO to one or more products and/or by-products and/or waste products, wherein the methanol carbonylation vessel 10 is configured to receive at least a portion of the methanol and/or CO from the methanol synthesis vessel 6;

f) means to pass at least a portion of the methanol and/or CO of step (b) from the methanol synthesis vessel 6 to the methanol carbonylation vessel 10;

g) means to pass at least a portion of the one or more products and/or byproducts and/or waste products from the methanol carbonylation vessel 10 to the bioreactor 4 for use as co-substrate(s) in the microbial fermentation;

h) a separation vessel for removing at least a portion of the one or more products and/or byproducts and/or waste products from stream exiting the methanol carbonylation vessel 10 prior to the stream being passed to the bioreactor 4;

i) a second bioreactor 8 containing a culture of one or more microorganisms, the bioreactor 8 configured to convert at least a portion of a hydrogen rich substrate steam to one or more acid(s) by microbial fermentation; and j) a means to pass a hydrogen rich substrate stream exiting the first bioreactor 4 to a second bioreactor 8; wherein the hydrogen rich substrate stream is a by-product of the fermentation reaction of step (d).

According to the embodiment shown, the methanol carbonylation vessel receives methanol and carbon monoxide. Acetic acid may be produced using methanol carbonylation using conventional methodology and apparatus as described hereinbefore. A person skilled in the art would recognise that alternative methods for producing acetic acid as described hereinbefore in the specification can be used in alternative embodiments of the system.

According to the invention, at least a portion of the products of the methanol carbonylation vessel are provided to a bioreactor. As shown, optionally, a separation step may be used to remove at least a portion of the products of the reactor. For example, at least some of the acetic acid may be harvested and diverted away from the bioreactor. The separation step may thus be used to harvest valuable or useful products of the reactor. The separator may also be used to remove any components of the stream output by the reactor that may be detrimental to the fermentation reaction. For example, it may be desirable to remove at least a portion of the methanol produced in the reactor. Other intermediate processing steps may additionally or alternatively be used as desired.

The carbon monoxide and/or methanol fed to the methanol carbonylation vessel may be provided as a waste gas stream of an industrial process. The same or a different waste gas stream may be used to, at least in part, feed the fermentation in the bioreactor. The use of waste gas streams captures carbon from waste streams that would otherwise typically be flared or otherwise discharged to the air. Thus, the invention provides for the capture of carbon that would otherwise add to greenhouse gas concerns.

Such arrangements can provide for improved fermentation by providing additional or alternative feedstock therefor. Additionally, or alternatively, improved acetic acid production may also result. For example, acetic acid may additionally be harvested from the bioreactor and/or one or more waste products of the bioreactor may be used to feed the acetic acid production process in the reactor.

At least the waste gas stream fed to the bioreactor may include CO and/or H2. The bioreactor contains a culture of one or more microorganisms capable of fermenting the CO and/or H2, as well as any products received from the reactor, to produce one or more alcohols.

Figure 2:
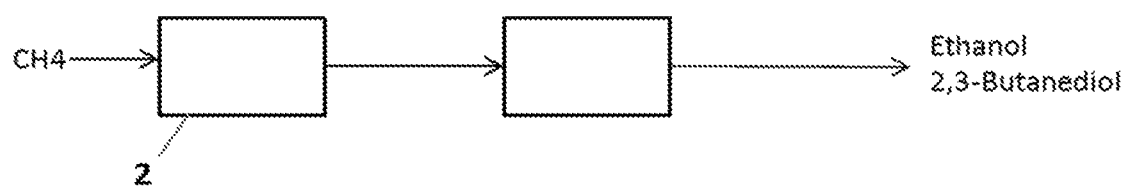
FIG. 2 shows the steam reformation of methane to produce a gas stream comprising CO and H2 which can be converted to methanol, wherein at least a portion of the gas stream comprising CO and H2 is diverted for fermentation to produce products such as ethanol, 2,3-butanediol and acetic acid.

The first aspect of the invention is shown in FIG. 2. According to the first aspect the invention provides a method for producing products from a gas stream used in the methanol production process. FIG. 2 shows a catalytic oxidation stage 2 for conversion of a gas stream comprising methane to a substrate stream comprising CO and H2. The substrate stream comprising CO and H2 is passed to the bioreactor 4 for conversion to one or more products by anaerobic fermentation.

Figure 3:
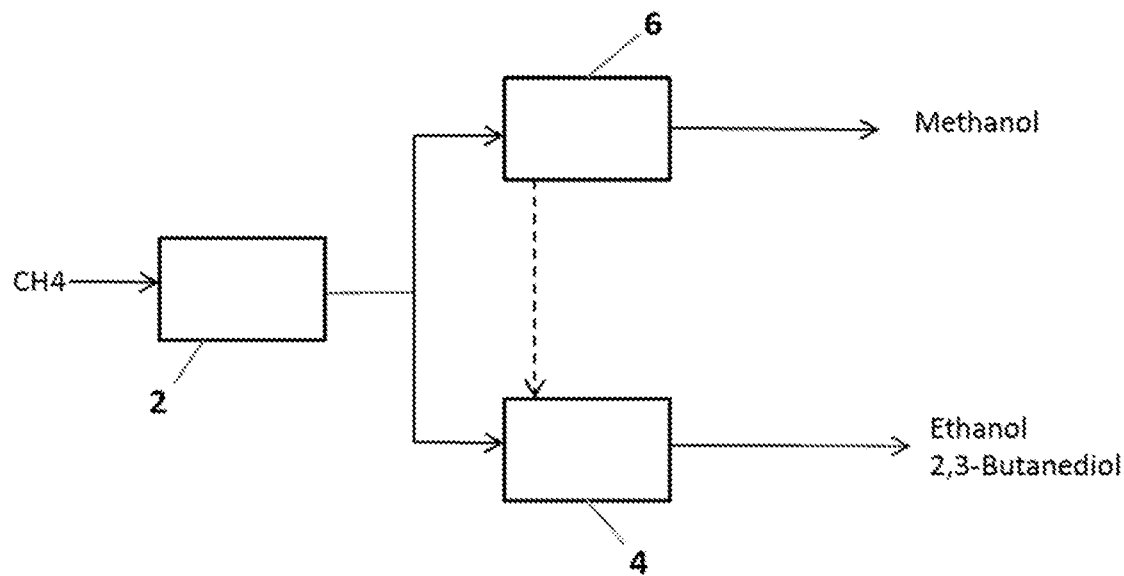
FIG. 3 shows a system and method according to a particular embodiment of the invention, wherein at least a portion of a gas stream comprising CO and H2 is passed to a methanol synthesis reaction vessel, and at least a portion of the gas stream comprising CO and H2 is passed to a bioreactor.

FIG. 3 shows a system according to a further aspect of the invention, wherein the system includes a catalytic oxidation stage 2 for the production of a substrate stream comprising CO and H2; a bioreactor 4 for the conversion of at least a portion of the substrate stream comprising CO and H2; and a methanol synthesis vessel 6 for the conversion of at least a portion of the substrate stream comprising CO and H2 to methanol. As shown in FIG. 3, a substrate stream comprising CO and H2 can be passed to the bioreactor 4 prior to and/or after the substrate stream has been passed to the methanol synthesis vessel 6.

Figure 4:
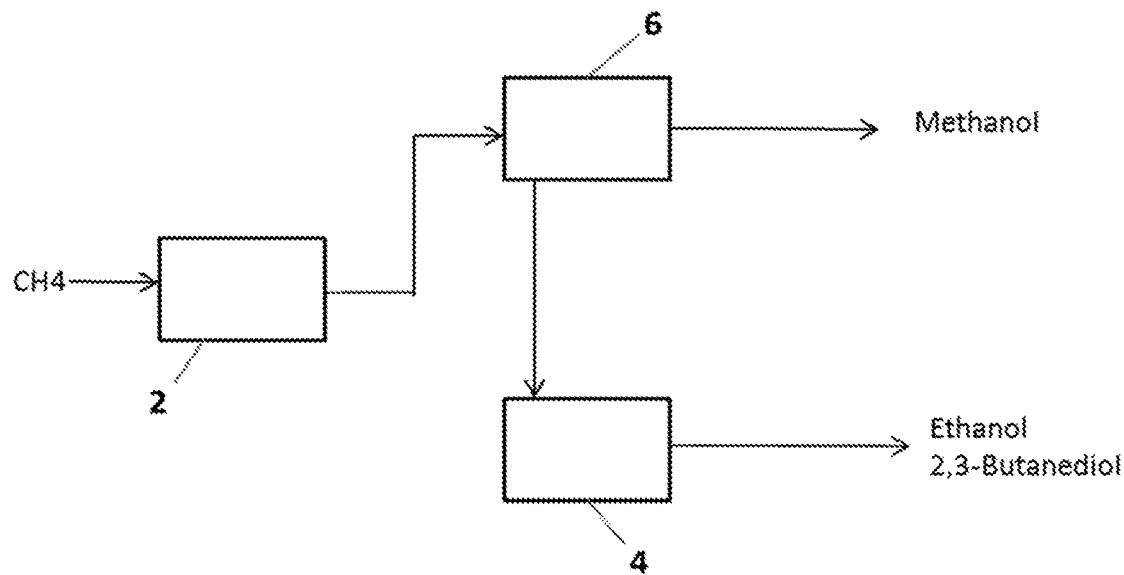
FIG. 4 shows a system and method according to a particular embodiment of the invention, wherein a gas stream comprising CO and H2 is recycled through a methanol synthesis reaction vessel, wherein at least a portion of the gas stream comprising CO and H2 exiting the methanol synthesis vessel is diverted to a fermentation process to produce products such as ethanol, 2,3-butanediol and acetic acid.

FIG. 4 shows an alternative embodiment of the system of FIG. 3, wherein the substrate stream comprising CO and H2 is passed to the methanol synthesis vessel 6 prior to being passed to the bioreactor 4.

Figure 5:
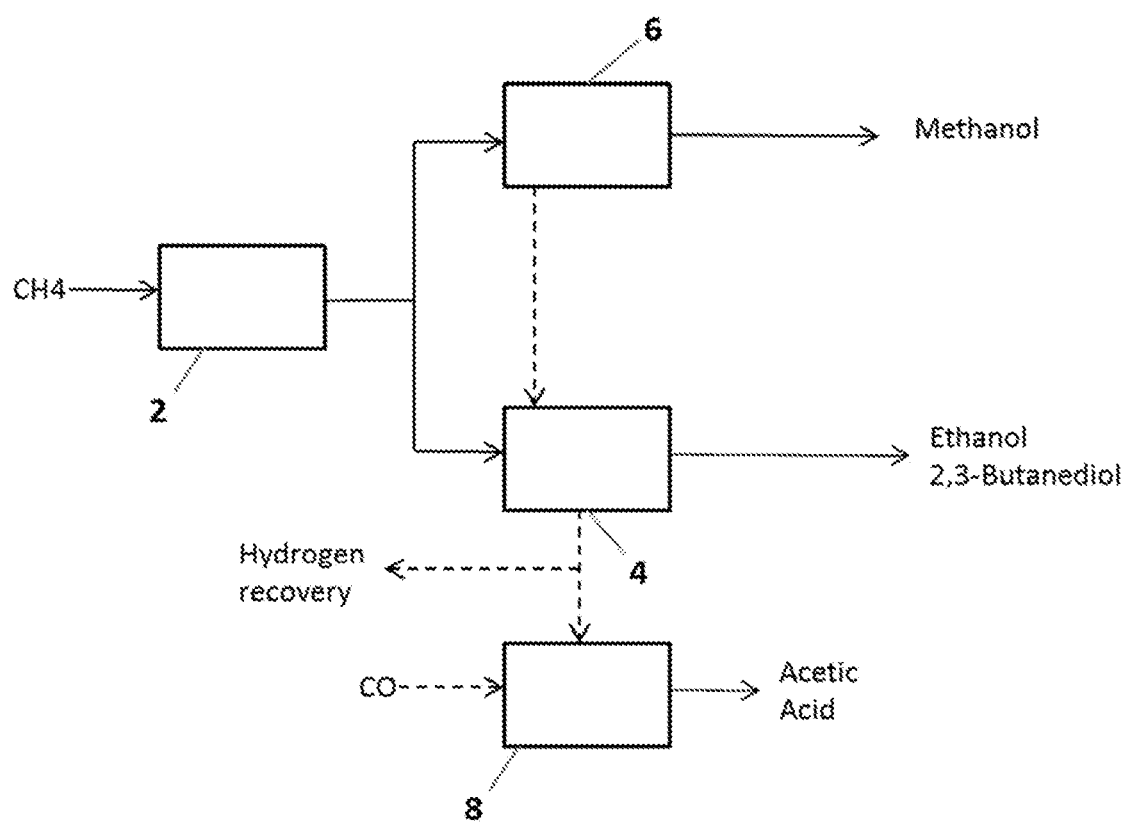
FIG. 5 shows a system and method according to a particular embodiment of the invention, wherein a hydrogen rich gas exiting a first bioreactor is passed into a second bioreactor.

FIG. 5 shows a further embodiment of the system of FIG. 3, further comprising a second bioreactor 8. The second bioreactor 8 is configured to receive a hydrogen rich gas stream exiting the first bioreactor 4. They hydrogen rich gas stream comprises H2 and optionally CO2. FIG. 5 depicts the optional recovery of hydrogen from the hydrogen rich gas stream prior to the stream entering the second bioreactor 8. FIG. 5 further shows the optional passing of CO2 from another source to the second bioreactor 8. The bioreactor 8 is preferably configured for acetic acid production.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, heading, or the like are provided to aid the reader's comprehension of this document, and should not be read as limiting the scope of the present invention. The entire disclosures of all applications, patents and publications cited herein are herein incorporated by reference.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A method comprising:
   a. converting a gas stream comprising methane to a substrate stream comprising CO and $H_2$;
   b. passing a portion of the substrate stream to a methanol synthesis process to convert at least a portion of the CO and $H_2$ in the substrate stream to methanol;
   c. passing a portion of an exit stream comprising methanol and CO from the methanol synthesis process to a methanol carbonylation process to convert the methanol and CO to acetic acid;
   d. passing an exit gas stream comprising CO and $H_2$ from the methanol synthesis process to a first bioreactor containing a culture of at least one carboxydotrophic bacteria and anaerobically fermenting at least a portion of the exit gas stream comprising CO and $H_2$ from the methanol synthesis process to produce at least one product selected from alcohols, acids 2,3-butanediol and combinations thereof;
   e. passing an exit stream from the carbonylation process comprising acetic acid, by-products and waste products, to a separation vessel operated at conditions to produce an acetic acid product stream and a gaseous stream comprising CO;
   f. passing the gaseous stream comprising CO from step (e) to the first bioreactor;
   g. passing a portion of the substrate stream comprising CO and $H_2$ from step (a) to the first bioreactor;
   h. passing an exit gas stream from the first bioreactor comprising $H_2$ and $CO_2$, the exit gas stream being rich in $H_2$, to a second bioreactor comprising a culture of at least one carboxydotrophic bacteria and anaerobically fermenting at least a portion of the $H_2$ and $CO_2$ to acetic acid.

2. The method of claim 1, wherein the methane is converted to CO and $H_2$ by catalytic oxidation.

3. The method of claim 1, wherein the at least one product produced in step (d) is selected from ethanol, 2,3-butanediol, acetic acid and any combination thereof.

4. The method of claim 1, further comprising passing a $CO_2$ comprising stream to the second bioreactor.

5. The method of claim 1, wherein the carboxydotrophic bacteria of step (d) is selected from *Clostridium, Moorella, Carboxydothermus*, and any combination thereof.

6. The method of claim 5, wherein the carboxydotrophic bacteria is *Clostridium*.

7. The method of claim 6, wherein the carboxydotrophic bacteria is *Clostridium autoethanogenum*.

8. The method of claim 1, further comprising passing the $H_2$ rich exit gas stream from the first bioreactor to a recovery zone where at least a portion of the $H_2$ is recovered before passing the exit gas stream to the second bioreactor.

9. The method of claim 1, wherein the at least one carboxydotrophic bacteria of step (h) is selected from *Acetobacterium, Moorella, Clostridium, Ruminococcus, Eubacterium*, Butyribacterium, *Oxobacter, Methanosarcina, Desulfotomaculum*, and any combination thereof.

10. The method of claim 9, wherein the carboxydotrophic bacteria is *Acetobacterium*.

11. The method of claim 10, wherein carboxydotrophic bacteria is *Acetobacterium woodii*.

12. The method of claim 1, wherein the acetic acid produced by the carbonylation process is recovered.

* * * * *